(12) United States Patent
Shah et al.

(10) Patent No.: US 6,964,670 B1
(45) Date of Patent: Nov. 15, 2005

(54) EMBOLIC PROTECTION GUIDE WIRE

(75) Inventors: Niraj A. Shah, Mountain View, CA (US); Joann Heberer, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 525 days.

(21) Appl. No.: 09/615,157

(22) Filed: Jul. 13, 2000

(51) Int. Cl.$^7$ .............................................. A61M 29/00
(52) U.S. Cl. ..................................... 606/200; 623/1.11
(58) Field of Search ........................................ 606/200

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |

(Continued)

FOREIGN PATENT DOCUMENTS

| | | |
|---|---|---|
| EP | 0 472 334 A1 | 2/1992 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |

*Primary Examiner*—Vy Q. Bui
(74) *Attorney, Agent, or Firm*—Fulwider, Patton, Lee & Utecht LLP

(57) ABSTRACT

A sheath attached to a guide wire, a tubular shaft member slidable on the guide wire and a filtering assembly constricted within the sheath are movable in a vessel to a position distal to a lesion in the direction of fluid flow. The filtering assembly may be formed from a plurality of angularly spaced splines and a mesh disposed on the splines having properties of passing fluid in the vessel while blocking the passage of emboli in the fluid. The splines may be provided with shape memory for expanding against the wall of the vessel when released from constriction by the sheath. The sheath may be moved relative to the filtering assembly and the support member to release the filter for expansion against the vessel wall. An interventional device can be used to treat the lesion. Any emboli released into the vessel as a result of the interventional treatment are blocked by the filter member while fluid is allowed to pass there through.

26 Claims, 4 Drawing Sheets

U.S. PATENT DOCUMENTS

| | | | |
|---|---|---|---|
| 5,071,407 A | 12/1991 | Termin et al. | |
| 5,092,839 A | 3/1992 | Kipperman | |
| 5,100,425 A | 3/1992 | Fischell et al. | |
| 5,102,415 A | 4/1992 | Guenther et al. | |
| 5,108,419 A | 4/1992 | Reger et al. | |
| 5,152,777 A | 10/1992 | Goldberg et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,383,887 A | 1/1995 | Nadal | |
| 5,421,832 A | 6/1995 | Lefebvre | |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A * | 9/1998 | Daniel et al. | 606/159 |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maahs | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A * | 6/1999 | Tsugita et al. | 128/898 |
| 5,941,896 A | 8/1999 | Kerr | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,013,093 A | 1/2000 | Nott et al. | |
| 6,152,946 A | 11/2000 | Broome et al. | |
| 6,171,327 B1 * | 1/2001 | Daniel et al. | 606/159 |
| 6,171,328 B1 * | 1/2001 | Addis | 606/200 |
| 6,179,859 B1 * | 1/2001 | Bates et al. | 606/114 |
| 6,290,710 B1 * | 9/2001 | Cryer et al. | 606/159 |
| 6,322,577 B1 | 11/2001 | McInnes | |
| 6,383,193 B1 * | 5/2002 | Cathcart et al. | 606/108 |
| 6,383,206 B1 * | 5/2002 | Gillick et al. | 606/114 |

* cited by examiner

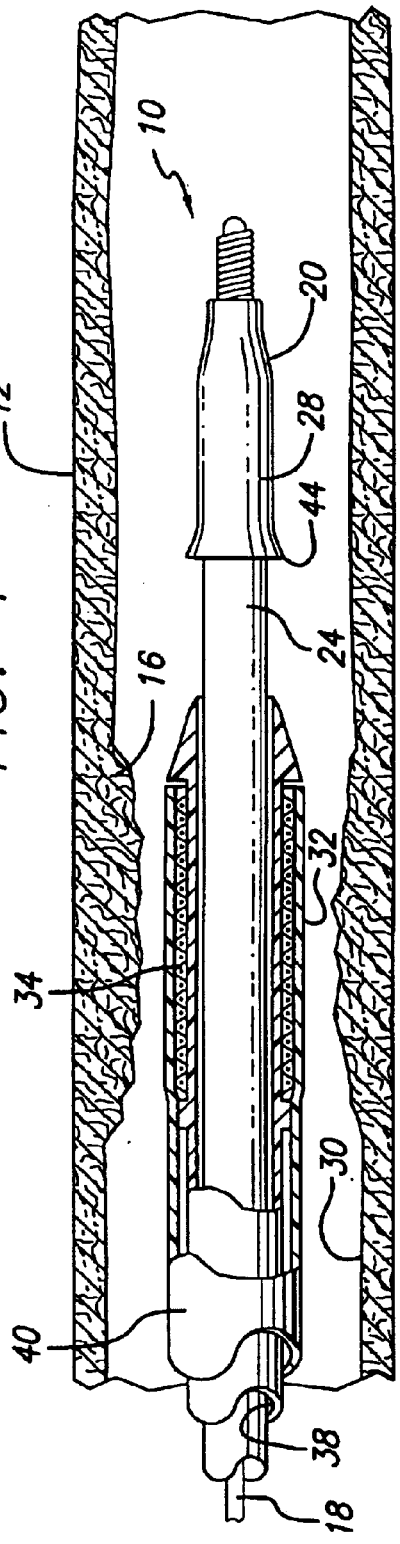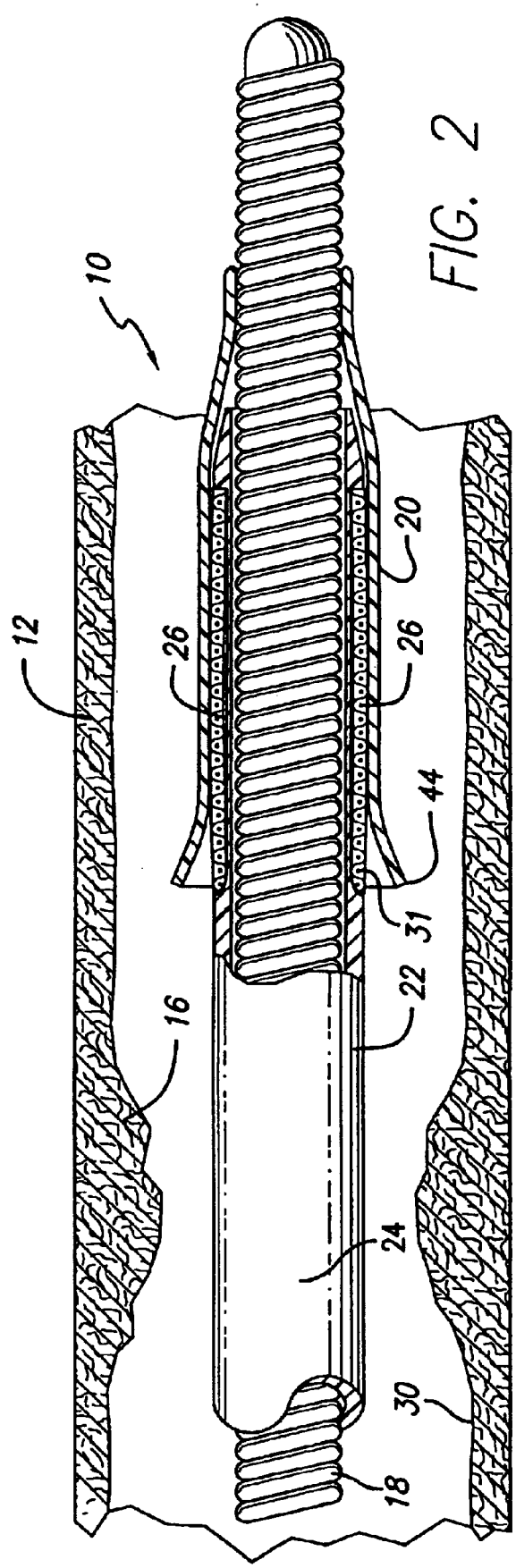

EMBOLIC PROTECTION GUIDE WIRE

BACKGROUND OF THE INVENTION

This invention relates to a device for, and methods of, trapping and removing emboli in a body vessel. The device and method of this invention are especially adapted to be used in preventing emboli in blood from passing through a vessel such as an artery.

In recent years, numerous procedures have been adapted for expanding blood vessels (e.g. arteries), at the positions of lesions in the blood vessels, so that blood can flow through the blood vessels without obstruction from the lesions. In the process of expanding such blood vessels at the positions of the lesions, embolic particles/debris may become detached from the lesions and enter the bloodstream and subsequently migrate through the patient's vasculature to cut off or reduce the amount of oxygenated blood being supplied to sensitive organs such as the brain and heart, which may induce trauma.

Procedures have also been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of emboli to blood vessels leading to the patient's brain, thereby preventing strokes from occurring.

Such filters are usually delivered in a collapsed position through the patient's vasculature and are then expanded once in place in the patient's blood vessel to trap the emboli. After emboli have been trapped, the filter is collapsed and removed (with the trapped emboli) from the vessel. Unfortunately, it is possible for some of the trapped emboli to escape from the filter during the time that the filter is being collapsed and/or removed from the blood vessel. When an interventional procedure is being performed in a carotid artery, even a trace release of emboli can be damaging. For these reasons, attempts to treat lesions in the carotid arteries have been somewhat limited due to the danger presented if all of the embolic debris is not collected during the procedure.

Therefore, in light of the above, it would be desirable for a device and method which can be utilized to treat an occluded vessel and trap any emboli that may be formed during the vascular procedure. Such a device and method must also prevent the emboli from escaping from the filter during the time that the filter is being collapsed and/or removed from the blood vessel (e.g. the carotid arteries). Although considerable progress has been made in recent years in providing a satisfactory filter, it would still be desirable to provide a filter which is simple, cost efficient and trustworthy in construction, is easy to deploy and remove from the patient's vasculature with little or no adverse impact or immunological response to the patient. Also, such a device should have a thin profile to reach tight distal lesions in the patient's vasculature.

SUMMARY OF THE INVENTION

The present invention is directed to a filtering device for trapping and removing emboli from a body vessel (e.g. an artery). In one embodiment of the invention, a sheath attached to a guide wire maintains a filtering assembly in a collapsed position until the filtering assembly is ready to be deployed in the patient's vasculature. The filtering assembly is attached to a tubular shaft member which is slidable over the guide wire to move the filtering assembly out of the sheath when the filtering assembly is to be deployed and to retract the sheath back over the filtering assembly when the assembly is to collapsed and removed from the vessel. The filtering assembly may be formed from a plurality of angularly spaced splines and a filter member made from mesh or other suitable filtering material. The filter member is disposed on the splines and has properties of passing fluid in the vessel while blocking the passage of emboli in the fluid. The splines may be made from a shape-memory material which allows the splines to self expand once the sheath is removed. The splines expand against the wall of the vessel when released from the collapsed or compressed position to deploy the filter member in the vessel in order to provide the necessary emboli filtration within the vessel.

An interventional device, such as an expandable member (e.g., a stent delivery catheter) and a stent, can be disposed in the vessel to treat the lesion and open the vessel at the lesion position. Any suitable interventional device can be used with the present invention. After the interventional device has performed the procedure, the embolic protection filter is collapsed and removed from the vessel. Emboli created during the interventional procedure are released into the fluid flow (e.g. bloodstream) and are trapped within the filtering assembly.

In one aspect of the invention, the tubular shaft member can be made from a nickel titanium (NiTi) hypotube. The splines can also be made from a nickel-titanium (NiTi) alloy or other shape memory material. The splines are biased to the deployed or expanded position so that once the sheath is removed, the splines will expand radially outward to abut against the wall of the vessel to provide a tight seal which prevents fluid and emboli from passing between the filter member and vessel wall. When the device is to be collapsed and removed from the patient, the physician simply moves the sheath back over the filtering assembly causing the splines to collapse, along with the filter member, thus trapping the emboli in the filter member. The lengths of the splines and filter member should be sufficiently long so that the filtering assembly traps the emboli deep within the distal end of the filter member. This helps prevent any backflow of trapped emboli into the vessel when the filtering assembly is being collapsed. Thereafter, the entire device can be removed from the patient.

These and other advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a preferred embodiment of an embolic protection guide wire for trapping and removing emboli released in a body vessel, along with an interventional device (a stent delivery catheter and self-expanding stent), positioned within a body vessel;

FIG. 2 is an enlarged fragmentary elevational view, primarily in section, of the embodiment of FIG. 1 showing in additional detail the filtering assembly at a position in the vessel which is distal and downstream from the lesion, the filter assembly being shown covered by a sheath in the collapsed or compressed position;

DETAILED DESCRIPTION OF THE PREFERRED EMBODIMENTS

Figure 3:
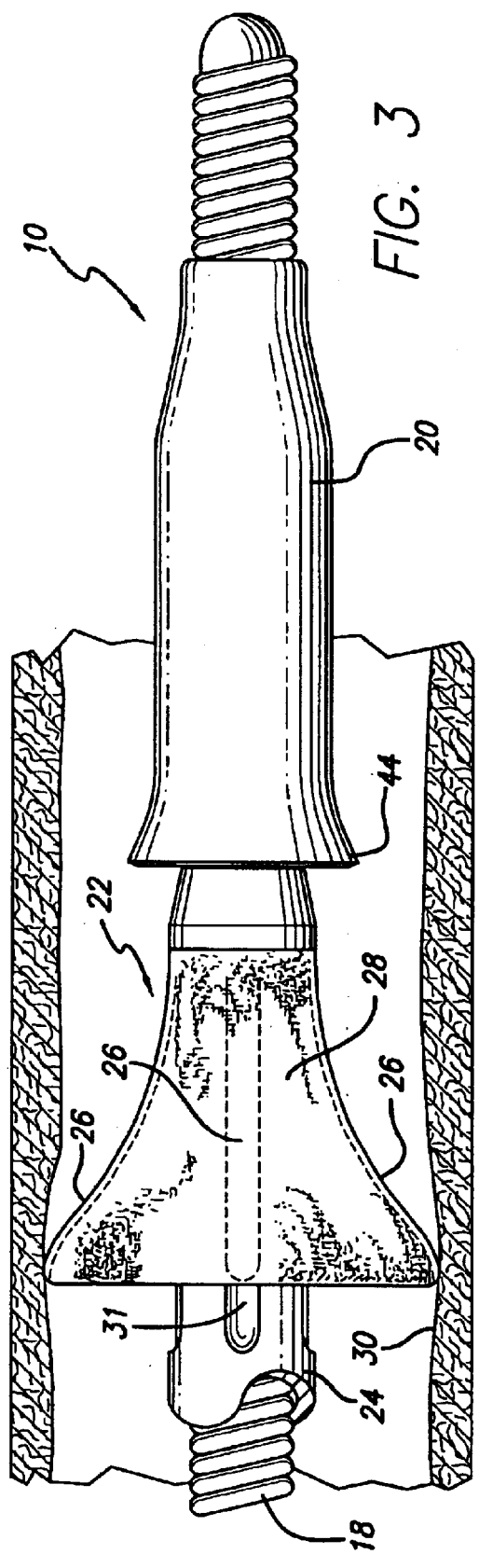
FIG. 3 is an enlarged fragmentary elevational view, primarily in section, of the filtering assembly of FIG. 2, the filtering assembly being shown withdrawn from the sheath and expanded against the wall of the vessel to trap emboli in the fluid.
Figure 4:
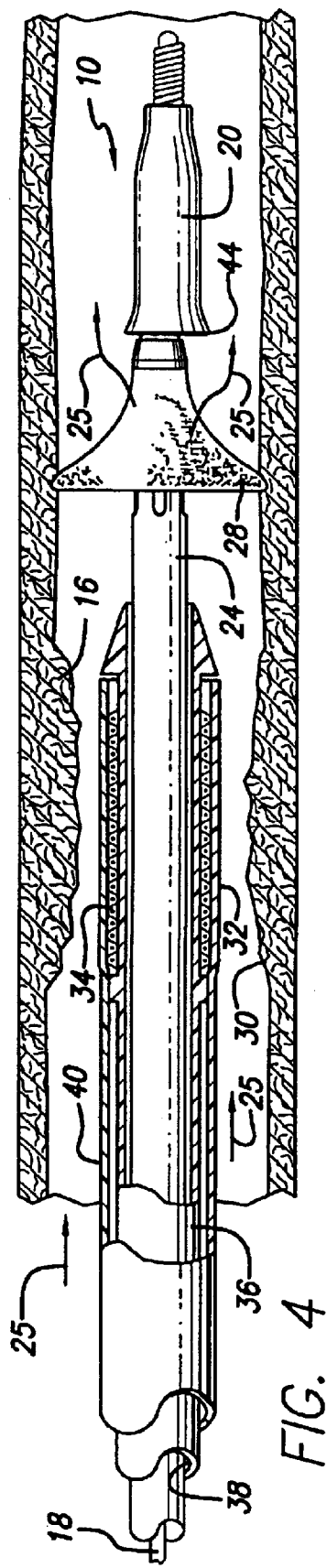
FIG. 4 is an enlarged fragmentary elevational view, primarily in section, of the filtering assembly in the expanded position and additionally showing the stent delivery catheter and stent in position across the lesion.

A device generally indicated at 10 and constituting one preferred embodiment of the present invention traps and removes emboli from a body vessel. The device 10 is adapted to be disposed in a blood vessel 12 to pass the fluid (blood) in the vessel and block the passage of emboli 14 (FIG. 5) in the fluid. The emboli 14 are produced when the blood vessel 12 is treated at the position of a lesion 16 during an interventional procedure such as, a balloon angioplasty procedure, a stenting procedure, an atherectomy procedure and the like. The present invention is designed to collect and remove such embolic debris from the artery to prevent the blockage of the smaller vessels downstream from the area of treatment. The device 10 is especially adapted to prevent blockage of small blood vessels leading to the brain which, if blocked, can result in the patient suffering a stroke.

The device 10 includes a flexible guide wire 18 on which is mounted a sheath 20 made from a suitable material such as a polymer, which will maintain the shape and flexibility of the sheath 20 may be dependent upon the size and location of the lesions that the sheath 20 has to cross. A filtering assembly 22 attached to a tubular shaft member 24 is disposed in a collapsed or compressed position within the sheath 20. This tubular shaft member 24 is slidably disposed on the guide wire 18 and may be made from a material such as nickel titanium (NiTi) alloy or any other material which has sufficient axial strength and flexibility to move the filtering assembly 22 along the guide wire into tortuous anatomy. For example, a hypotube made from Nitinol would be suitable since it possess sufficient strength, has adequate flexibility to be advanced through tortuous anatomy, and can be made with a thin wall to reduce the overall profile of the device. This material also is advantageous because it is able to withstand buckling.

The filtering assembly 22 is attached to the tubular shaft member 24 for slidable movement along the guide wire 18. The filtering assembly 22 may be formed from a plurality of annularly spaced splines 26 (FIG. 3) supporting a filter member 28. The filtering assembly 22 is designed to be self expanding from the collapsed position to an expanded position within the vessel 12. In the collapsed position, the filtering assembly 22 would be disposed within the sheath 20. In the expanded position, the filtering assembly 22 would flare radially outward to engage the wall 30 of the vessel 12. The splines 26 may be formed from a material having shape memory which causes the splines 26 to expand against the wall of the vessel 12 when the filtering assembly 22 is released from the sheath 20. Nitinol is one suitable material which could be used to create the splines 26. The filter member 28 may be made from a mesh or suitable filtering material. For example, the filter member 28 may be made from a thin polymer having small openings to pass the fluid in the vessel 12 while blocking the passage of the emboli 14 in the fluid. The filter member 28 may be coated with an anti-thrombotic agent to minimize blockage of the filter media by thrombosis. The filter material could also be non-porous. The ability of the embolic protection guide wire and filter to deploy and retract multiple times could allow the physician to periodically retract the device to allow blood flow downstream from the filer. Such non-porous materials would include polymeric materials well-known in medical catheter design. Each of the splines 26 could be positioned in a recess 31 formed on the tubular shaft member 24 when in the collapsed position to reduce the overall profile of the filtering assembly.

An interventional device, such as a stent delivery catheter 32 and a self-expanding stent 28, can be utilized to treat the lesion 16 and open up the artery 12 to increase blood flow therethrough. This stent delivery catheter 32 and the stent 34 may be constructed in a manner well known in the art. It should be appreciated that other interventional devices can be used with the embolic protection guide wire. For example, balloon expandable stents, balloon angioplasty catheters, atherectomy devices and the like can be used to treat the stenosis as well.

The delivery catheter 32 and the stent 34 may be disposed at the position of the lesion 16 as shown schematically in FIGS. 1 and 4–6. In the drawings, small arrows 25 indicate the direction of the fluid flow within the vessel 12. The stent delivery catheter 32 includes an inner tubular member 36 onto which the compressed or collapsed stent 34 is mounted. This inner tubular member 36 includes an inner lumen 38 which allows the stent delivery catheter 32 to be disposed over the device 10 in a co-axial arrangement. This allows the stent delivery catheter 32 to be delivered to the area of treatment using over-the-wire techniques. An outer restraining sheath 40 extends over the inner tubular member 36 in a co-axial arrangement and is used to restrain the collapsed stent 34 until it is ready to be deployed. Both the outer retraining sheath 40 and inner tubular member 36 have proximal ends (not shown) which extent outside of the patient. In use, the physician moves the proximal ends to retract the restraining sheath the necessary length to deploy the self-expanding stent 34. Once the stent is positioned across the lesion 16, the restraining sheath 40 can be retracted to expose the stent 34 and allow it to self expand against the wall 30 of the vessel 12. The opening in the vessel 12 is maintained by the stent 34 even after the delivery catheter 32 is withdrawn from the vessel 12.

The filtering assembly 22 is initially provided in the collapsed position within the sheath 20 as is shown schematically in FIGS. 1 and 2. As a first step, the filter assembly 22 is disposed in the vessel 12 to a position past the lesion 16 in the direction of the fluid flow (downstream of the lesion 16). When the filtering assembly 22 has been properly positioned in the vessel 12, the sheath 20 is moved in a direction to expose the filtering assembly 22. This causes the splines 26 and the filter member 28 to expand against the wall of the vessel 12. This is shown schematically in FIG. 3. In this position, the filter member 28 passes the fluid in the vessel 12 but blocks the passage of the emboli 14 in the fluid. The direction of the fluid flow in the vessel 12 is indicated schematically by solid arrows 25.

The stent delivery catheter 32 and stent 34 are then positioned in the vessel 12 across the lesion 16. This is shown schematically in FIG. 4. The stent 34 expands against the wall of the vessel 12, thereby opening the vessel at the position of the lesion 16 to increase the flow of fluid through the vessel. The expansion of the stent 34 against the wall of the vessel 12 is indicated schematically in FIG. 5. As indicated schematically in FIG. 5, the lesion 16 is compressed against the wall 30 of the vessel 12, thereby expanding the opening in the vessel at the position of the lesion 16.

Figure 5:
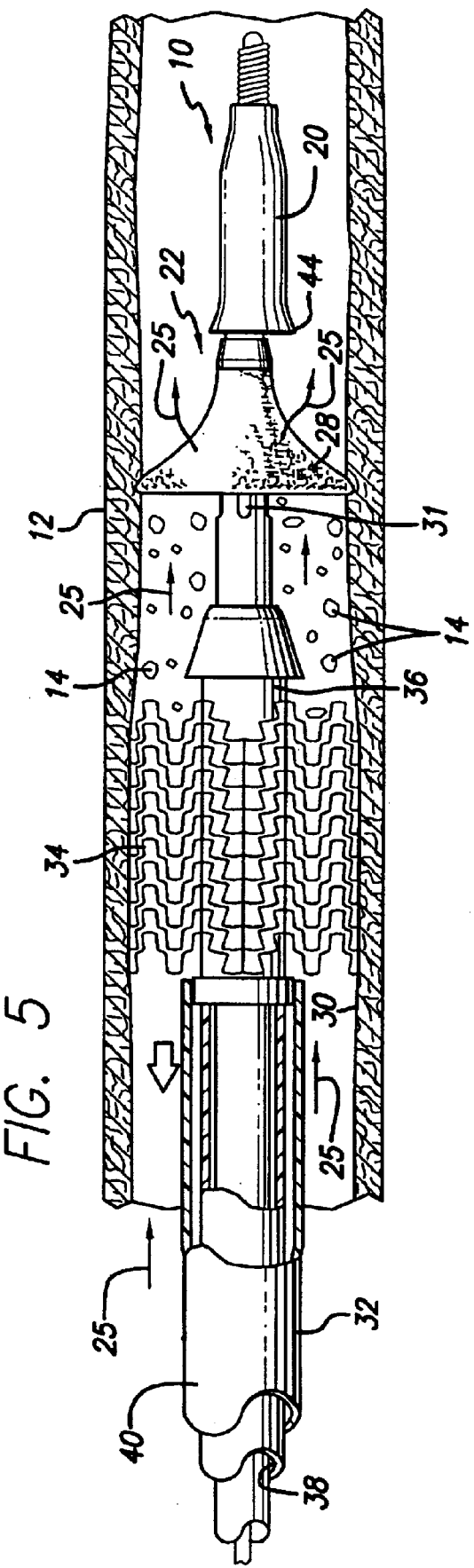
FIG. 5 is an enlarged fragmentary elevational view, primarily in section, of the filtering assembly in the expanded position and also showing the stent expanded against the vessel wall with the stent delivery catheter being withdrawn from the vessel.
Figure 6:
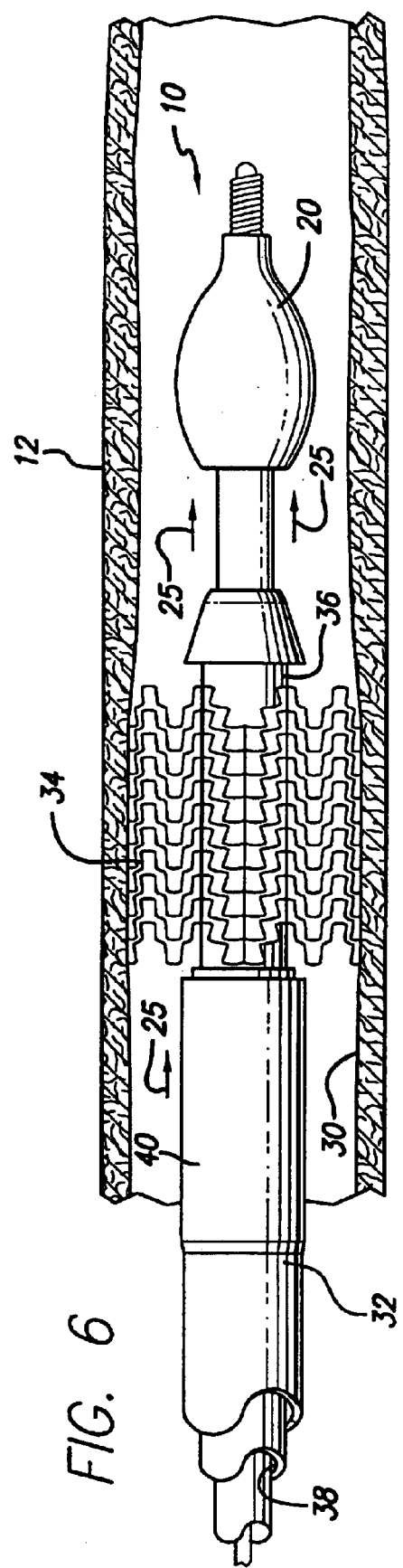
FIG. 6 is an enlarged fragmentary elevational view, primarily in section, showing the filtering assembly being disposed back to the collapsed position within the sheath with the trapped emboli contained within the filter member.
Figure 7:
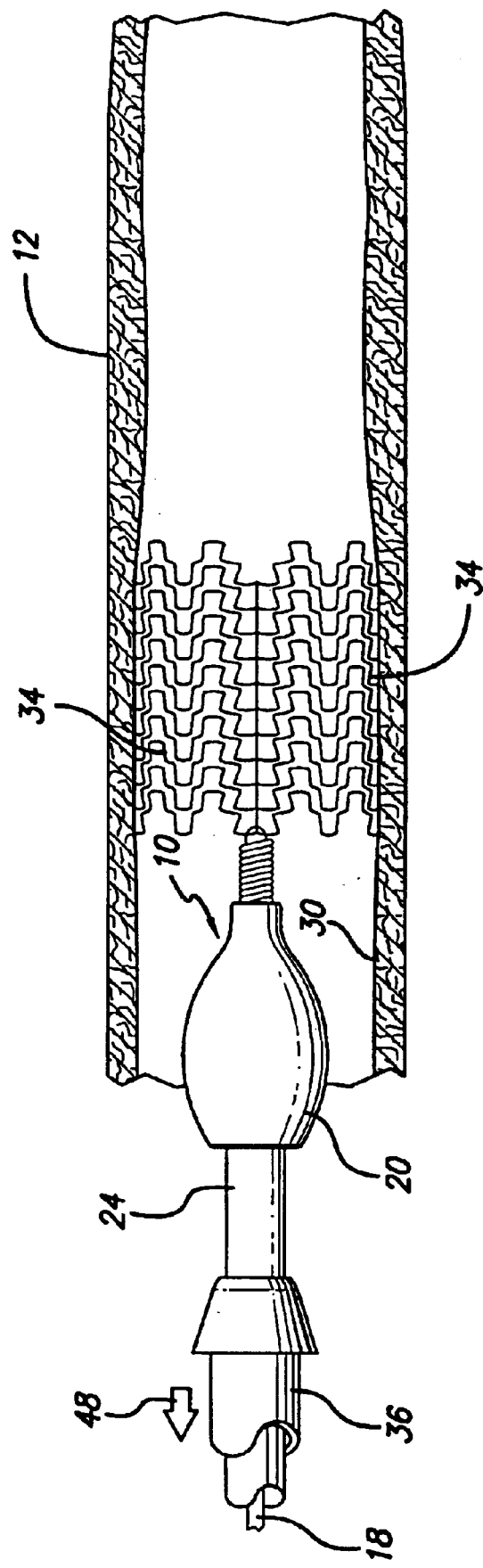
FIG. 7 is an enlarged fragmentary elevational view, primarily in section, showing the filtering assembly constricted within the sheath and being withdrawn from the vessel.

The expansion of the stent 34 against the lesion 16 may create emboli 14 as indicated schematically in FIG. 5. However, the emboli 14 are blocked by the filter member 28 from flowing through the mesh. When all of the emboli 14 have flowed to the filter member 28, the stent delivery catheter 32 is withdrawn. This is indicated schematically in FIGS. 6 and 7.

The filtering assembly 22 (with the trapped embolic debris retained by the filter member 28) is then moved in a direction to dispose the filtering assembly 22 back into the sheath 20. When this occurs, some buckling of the filtering assembly 22 and the tubular shaft member 24 may take place. As previously indicated, the tubular shaft member 24 and the splines 26 may be made from a suitable material such as a nickel titanium alloy. This material is advantageous because it has an ability to withstand buckling when the tubular shaft member 24 and the filtering assembly 22 are pushed back into the sheath 20. It should be appreciated that the filtering assembly 22 can also be made from any metal or polymer which has flexible properties and properties of withstanding buckling when being pushed back into the sheath 20.

The sheath 20 can be provided with a variable length to ensure that all of the embolic debris remains in the sheath when the tubular shaft member 24 and the filtering assembly 22 are pushed back into the sheath 20. The lengths of the splines and filter member should be sufficiently long so that a deep pocket is created that traps the emboli deep within the distal end of the filter member 28. This helps prevent any backflow of trapped emboli 14 into the vessel when the filtering assembly 22 is being collapsed. The sheath 20 may have a slightly flared proximal end 44 which helps to receive the distal end 46 of the filtering assembly 22. After the tubular shaft member 24 and the filtering assembly 22 have been pulled back into the sheath 20, the filtering assembly 22 can be withdrawn from the vessel 12. This is indicated schematically by a hollow arrow 48 in FIG. 7.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A device for passing fluid in a vessel while preventing emboli in the fluid from passing through the vessel, comprising:
   a steerable guide wire;
   a sheath fixedly attached to the guide wire;
   a tubular shaft member having a proximal and distal end which is movable along the guide wire; and
   a filtering assembly disposed on the tubular shaft member which is movable between a collapsed and expanded position, the filtering assembly being constricted within the sheath while in the collapsed position and expanded within the vessel when released from constriction within the sheath to become disposed against the vessel to pass fluid in the vessel while blocking the passage of emboli in the vessel, the filtering assembly including an expandable structure cut from a portion of the tubular shaft member.

2. The filtering device of claim 1, wherein:
the expandable structure of the filtering assembly includes a plurality of splines disposed in annularly spaced relationship to one another and a filter member is attached to the splines.

3. The filtering device of claim 2, wherein:
the splines are formed from a material having shape memory for disposition against the vessel when released from the sheath and
the filter member is formed from a material having properties of passing the fluid in the vessel while blocking the passage of emboli in the vessel.

4. The filtering device of claim 1, wherein:
the filtering assembly becomes disposed within the sheath when the tubular shaft member becomes disposed within the sheath.

5. The filtering device of claim 1, wherein:
the filtering assembly is self-deploying.

6. The filtering device of claim 2, wherein:
the splines are self-expanding.

7. The filtering device of claim 2, wherein:
the tubular shaft member has a recess for housing the splines when the filtering assembly is in the collapsed position.

8. The filtering device of claim 1, wherein:
the sheath is made from a polymer and has a length to ensure that all of the emboli remain in the sheath when the filtering assembly is moved from the expanded position back into the collapsed position within the sheath.

9. The filtering device of claim 1, wherein:
the filtering assembly has a length to ensure that all of the emboli remain in the filter member when the filtering assembly is moved from the expanded position back into the collapsed position within the sheath.

10. The filtering device of claim 1, wherein:
the filtering assembly has a memory for expanding against the vessel when the tubular shaft member and filtering assembly are displaced relative to the sheath so that they are no longer housed within the sheath.

11. The filtering device of claim 1, wherein:
the tubular shaft member is made from a material having flexible properties and properties of withstanding buckling.

12. The filtering device of claim 1, wherein:
the sheath has a flexibility and shape dependent upon the characteristics of the tortuous anatomy through which the sheath passes.

13. The filtering device of claim 1, wherein:
the filtering assembly has a plurality of splines which are made from a resilient material capable of withstanding buckling and which are spaced angularly from one another and which are provided with a memory for expansion to a particular configuration and which are covered with a filter member.

14. The filtering device of claim 1, wherein:
the sheath has distal and proximal ends, the distal end of the sheath being attached to a guide wire and the proximal end having a opening for receiving the filtering assembly.

15. The filtering device of claim 14, wherein:
the proximal end opening of the sheath is flared outward.

16. The filtering device of claim 1, wherein:
the tubular shaft member is made from hypotube formed from a nickel titanium alloy.

17. A method of passing fluid in a vessel and of preventing emboli in the fluid from passing through the vessel from a lesion in the vessel, including the steps of:
providing a filtering assembly having constricted and expanded positions and having properties in the expanded position of passing fluid while blocking the passage of emboli from the lesion, the filtering assembly being disposed on a tubular shaft member having a lumen for receiving a guide wire, the filtering assembly including an expandable structure cut from a portion of the tubular shaft member,
disposing the filtering assembly in a sheath fixedly attached to a steerable guide wire in the constricted position with the filtering assembly disposed in the sheath and movable relative to the sheath, the steerable guide wire being disposed and movable within the lumen of the tubular shaft member,
positioning the filtering assembly and the sheath in the vessel at a position past the lesion in the direction of the fluid flow in the vessel,
producing relative movement between the sheath and the filtering assembly in a direction to move the filtering assembly in the expanded position, and
expanding the opening in the vessel at the position of the lesion with an interventional device while the filtering assembly remains in the expanded relationship to provide for the operation of the filtering assembly in passing the fluid while blocking the passage of emboli created during the expansion of the opening in the vessel.

18. A method as set forth in claim 17, including the step of:
withdrawing the sheath and the filtering assembly from the vessel after the disposition of the filtering assembly in the sheath with the emboli disposed within the filtering assembly.

19. A method as set forth in claim 18, wherein:
the filtering assembly is disposed in a fixed relationship on the tubular shaft member and the tubular shaft member is a hypotube,
the hypotube is made from a flexible material having properties of withstanding buckling, and
the distal end of the hypotube becomes disposed within the sheath when the filtering assembly is placed into the sheath.

20. A method as set forth in claim 19, wherein:
the filtering assembly is formed from angularly spaced splines formed from a resilient material capable of withstanding buckling, and
the splines are covered with a filter member made from a material having properties of passing the fluid while blocking the passage of the emboli in the fluid.

21. A method as set forth in claim 17, wherein:
the filtering assembly is disposed in a fixed relationship on a hypotube,
the hypotube is made from a flexible material having properties of withstanding buckling, and
the distal end of the hypotube becomes disposed within the sheath when the filtering assembly is placed into the sheath.

22. A device for passing fluid in a vessel while preventing emboli in the fluid from passing through the vessel, comprising:
a guide wire;
a sheath attached to the guide wire;
a tubular shaft member movable along the guide wire in a co-axial arrangement; and
a self-expanding filtering structure cut from a portion of the tubular shaft member, the self-expanding filtering structure being movable between a collapsed portion within the sheath and an expanded position when released from the sheath and including a filter member attached thereto.

23. The filtering device of claim 22, wherein:
the self-expanding filtering structure includes a plurality of splines formed from a portion of the tubular shaft member.

24. The filtering device of claim 23, wherein:
a plurality of recesses are formed in the tubular shaft member for housing the plurality of splines when the filtering structure is placed in the collapsed position to reduce the profile of the filtering structure.

25. The filtering device of claim 23, wherein:
the plurality of splines are biased to the expanded position.

26. The filtering device of claim 22, wherein:
the tubular shaft member is a hypotube made from nickel-titanium alloy.

* * * * *

UNITED STATES PATENT AND TRADEMARK OFFICE
CERTIFICATE OF CORRECTION

PATENT NO. : 6,964,670 B1
DATED : November 15, 2005
INVENTOR(S) : Niraj A. Shah et al.

It is certified that error appears in the above-identified patent and that said Letters Patent is hereby corrected as shown below:

Title page,
Item [56], References Cited, U.S. PATENT DOCUMENTS, insert
-- 6,391,044   5/2002   Yadav et al. --.

Column 2,
Line 4, delete "is to collapsed" and insert -- is to be collapsed --.

Column 3,
Line 39, delete ", which will maintain the" and insert -- . The --.
Line 50, delete "possess" and insert -- possesses --.

Column 4,
Line 13, delete "filer" and insert -- filter --.
Line 43, delete "extent" and insert -- extend --.

Signed and Sealed this

Ninth Day of May, 2006

JON W. DUDAS
*Director of the United States Patent and Trademark Office*